US009675692B2

(12) United States Patent
Walsh et al.

(10) Patent No.: US 9,675,692 B2
(45) Date of Patent: Jun. 13, 2017

(54) STABILIZED FORMULATIONS CONTAINING ANTI-DLL4 ANTIBODIES

(71) Applicant: Regeneron Pharmaceuticals, Inc., Tarrytown, NY (US)

(72) Inventors: Scott Walsh, Tarrytown, NY (US); Daniel Dix, Lagrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 203 days.

(21) Appl. No.: 13/906,479

(22) Filed: May 31, 2013

(65) Prior Publication Data

US 2013/0323260 A1   Dec. 5, 2013

Related U.S. Application Data

(60) Provisional application No. 61/653,478, filed on May 31, 2012.

(51) Int. Cl.
*A61K 39/395* (2006.01)

(52) U.S. Cl.
CPC .. *A61K 39/39533* (2013.01); *A61K 39/39591* (2013.01)

(58) Field of Classification Search
None
See application file for complete search history.

(56) References Cited

U.S. PATENT DOCUMENTS

| | | | |
|---|---|---|---|
| 4,997,423 A | 3/1991 | Okuda et al. | |
| 5,016,784 A | 5/1991 | Batson | |
| 5,908,686 A | 6/1999 | Sudo et al. | |
| 6,171,586 B1 | 1/2001 | Lam et al. | |
| 6,267,958 B1 | 7/2001 | Andya et al. | |
| 6,286,699 B1 | 9/2001 | Sudo | |
| 6,645,635 B2 | 11/2003 | Muraki | |
| 6,875,432 B2 | 4/2005 | Liu et al. | |
| 7,001,892 B1 | 2/2006 | Chmielewski et al. | |
| 7,060,268 B2 | 6/2006 | Andya et al. | |
| 7,226,554 B2 | 6/2007 | Sudo et al. | |
| 7,488,806 B2 | 2/2009 | Papadopoulos et al. | |
| 7,534,868 B1 | 5/2009 | Papadopoulos et al. | |
| 7,608,261 B2 | 10/2009 | Furfine et al. | |
| 7,807,164 B2 | 10/2010 | Furfine et al. | |
| 7,919,593 B2 | 4/2011 | Papadopoulos et al. | |
| 8,092,803 B2 | 1/2012 | Furfine et al. | |
| 8,110,546 B2 | 2/2012 | Dix et al. | |
| 8,404,638 B2 | 3/2013 | Dix et al. | |
| 8,481,046 B2 | 7/2013 | Furfine et al. | |
| 2003/0092606 A1 | 5/2003 | L'Italien et al. | |
| 2003/0113316 A1 | 6/2003 | Kaisheva et al. | |
| 2003/0190316 A1 | 10/2003 | Kakuta et al. | |
| 2003/0202972 A1 | 10/2003 | Andya et al. | |
| 2004/0197324 A1 | 10/2004 | Liu et al. | |
| 2006/0217311 A1 | 9/2006 | Dix et al. | |
| 2011/0150905 A1 | 6/2011 | Papadopoulos et al. | |
| 2011/0217237 A1* | 9/2011 | Chen et al. | 424/9.1 |
| 2012/0178683 A1 | 7/2012 | Dix et al. | |
| 2013/0261056 A1 | 10/2013 | Dix et al. | |
| 2013/0274189 A1 | 10/2013 | Furfine et al. | |

FOREIGN PATENT DOCUMENTS

| | | |
|---|---|---|
| EP | 1314437 A1 | 5/2003 |
| EP | 1475100 A4 | 5/2005 |
| WO | 93/00807 A1 | 1/1993 |
| WO | 98/22136 A2 | 5/1998 |
| WO | 98/56418 A1 | 12/1998 |
| WO | 2004/055164 A2 | 7/2004 |
| WO | 2005/072772 A1 | 8/2005 |
| WO | 2006/044908 A2 | 4/2006 |
| WO | 2006/104852 A2 | 10/2006 |
| WO | 2006/138181 A2 | 12/2006 |
| WO | 2007/149334 A2 | 12/2007 |
| WO | 2008/049897 A1 | 5/2008 |
| WO | 2008/076379 A2 | 6/2008 |
| WO | 2010/102241 A1 | 9/2010 |
| WO | 2011/061712 A1 | 5/2011 |
| WO | 2011/109298 A2 | 9/2011 |

OTHER PUBLICATIONS

Chang et al. (1996) "Physical Factors Affecting the Storage Stability of Freeze-Dried Interleukin-1 Receptor Antagonist: Glass Transition and Protein Conformation" Arch. Biochem. Biophys. 331(2):249-258.
Daugherty and Msrny (2006) "Formulation and Delivery Issues for Monoclonal Antibody Therapeutics" Adv. Drug Delivery Reviews 58:686-706.
Gokarn et al. (2008) "Self-Buffering Antibody Formulations" J. Pharm. Sci. 97(8):3051-66.
He et al. (2010) "High Throughput Thermostability Screening of Monoclonal Antibody Formulations" Journal of Pharmaceutical Sciences 99(4):1707-1720.
He et al. (2011) "High-Throughput Assessment of Thermal and Colloidal Stability Parameters for Monoclonal Antibody Formulations" Journal of Pharmaceutical Sciences 100(12):5126-5141.
Sainsin and Harris (Sep. 2007) "Anti-Dll4 Therapy: Can We Block Tumour Growth By Increasing Angiogenesis?" Trends in Molecular Medicine 13(9):389-395.
Shutter et al. (2000) "Dll4, a Novel Notch Ligand Expressed in Arterial Endothelium" Genes Develop. 14:1313-1318.
Wang (1999) "Instability, Stabilization, and Formulation of Liquid Protein Pharmaceuticals" Int'l J. Pharmaceutics 185(2):129-188.

(Continued)

*Primary Examiner* — Yunsoo Kim
(74) *Attorney, Agent, or Firm* — McCarter & English, LLP; Cristin H. Cowles; Deborah L. Nagle

(57) ABSTRACT

The present invention provides pharmaceutical formulations comprising an antibody that specifically binds to human delta-like ligand 4 (Dll4). The formulations may contain, in addition to an anti-Dll4 antibody, a phosphate buffer, an organic cosolvent, a disaccharide, and a salt. The pharmaceutical formulations of the present invention exhibit a substantial degree of antibody stability after storage for several months and after being subjected to thermal and other physical stress.

16 Claims, No Drawings

(56) References Cited

OTHER PUBLICATIONS

International Serach Report with respect to PCT/US2013/043516, mailed Sep. 12, 2013.

* cited by examiner

STABILIZED FORMULATIONS CONTAINING ANTI-DLL4 ANTIBODIES

RELATED APPLICATIONS

This patent application claims priority to U.S. Provisional Patent Application No. 61/653,478, which was filed on May 31, 2012 and which is incorporated herein by reference in its entirety.

FIELD

The present invention relates to the field of therapeutic antibody formulations. More specifically, the present invention relates to the field of pharmaceutical formulations comprising an antibody that specifically binds to human delta-like ligand 4 (Dll4).

SEQUENCE LISTING

An ST.25 compliant computer readable text file of a sequence listing is filed concurrently with the present specification according to 37 C.F.R. §1.821(e). The contents of the text file are herein incorporated by reference. A paper copy of the sequence listing, which pursuant to 37 C.F.R. §1.821(f) is identical in content to the ST.25 compliant computer readable text file, is included as part of the present specification and is herein incorporated by reference.

BACKGROUND

The Notch-signaling pathway is a system for cell-to-cell communication used by a wide range of eukaryotes for many biological processes, such as differentiation, proliferation, and homeostasis. Delta like 4 (Dl4) or delta-like ligand 4 (Dll4) (hereinafter "Dll4") is a member of the Delta family of Notch ligands which exhibits highly selective expression by vascular endothelium (Shutter et al. (2000) Genes Develop. 14:1313-1318). Dll4 is a ligand for Notch receptors, including Notch1 and Notch 4. The amino acid sequence for human Dll4 is depicted in SEQ ID NO:9. Given the important role that the Dll4-Notch signaling pathway plays in the regulation of angiogeneisis and its implication in human health and medicine, it is desired to develop and deploy Dll4-based medicaments. One such Dll4-based medicament is a therapeutic antibody specific to Dll4.

Methods to produce antibodies useful as human therapeutics include generation of chimeric antibodies and humanized antibodies (see, for example, U.S. Pat. No. 6,949,245). See, for example, WO 94/02602 (Abgenix) and U.S. Pat. No. 6,596,541 (Regeneron Pharmaceuticals), which publications are herein specifically incorporated by reference, describing methods of generating nonhuman transgenic mice capable of producing human antibodies. U.S. Pat. Nos. 7,488,806, 7,534,868, and 7,919,593, and U.S. Patent Application No. U.S. 2011-0150905A1 disclose antibodies to human Dll4, and are incorporated in their entirety herein by reference.

Therapeutic antibodies must be formulated in a manner that not only makes the antibodies suitable for administration to patients, but also in a manner that maintains their stability during storage and subsequent use. For example, therapeutic antibodies in liquid solution are prone to fragmentation, precipitation, aggregation, and undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, and the visual quality or appeal of the formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients.

Antibodies to Dll4 are one example of a therapeutically relevant macromolecule that requires proper formulation. Although some anti-Dll4 antibodies are known, there nonetheless remains a need in the art for novel pharmaceutical formulations comprising anti-Dll4 antibodies that are sufficiently stable and suitable for administration to patients.

SUMMARY

The present invention satisfies the aforementioned need by providing pharmaceutical formulations comprising a human antibody that specifically binds to human delta-like ligand 4 (Dll4).

In one aspect, a liquid pharmaceutical formulation is provided, comprising: (i) an antibody that specifically binds to Dll4; (ii) a buffer; (iii) an organic cosolvent; and (iv) thermal stabilizers.

In one embodiment, the antibody is provided at a concentration from about 20±3 mg/mL to about 75±11.25 mg/mL. In another embodiment, the antibody is provided at a concentration of about 25 mg/mL±3.75 mg/mL. In another embodiment, the antibody is provided at a concentration of about 50 mg/mL±7.5 mg/mL.

In one embodiment, exemplary anti-Dll4 antibodies of the invention comprise HCDR1, HCDR2, HCDR3, LCDR1, LCDR2 and LCDR3 domains having the respective amino acid sequences of SEQ ID NO: 2, 3, 4, 6, 7 and 8 (e.g., REGN421). In one embodiment, the antibody comprises the CDR sequences contained within an HCVR having an amino acid sequence of SEQ ID NO:1, and an LCVR having an amino acid of SEQ ID NO:5.

In one embodiment, the pH of the liquid formulation is about pH 5.0 to about pH 6.6; pH 6.0±0.5, pH 6.0±0.4, pH 6.0±0.3, pH 6.0±0.2, pH 6.0±0.1, pH 6.0±0.05, pH 6.0±0.01, or pH 6.0. In a specific embodiment, the pH of the liquid formulation is about pH 6.0±0.5. In one embodiment, the buffer has an effective buffering range of about pH 5.8 to about pH 8.0; or about pH 6.0 to about 7.5. In one embodiment, the buffer has a pKa of about 6.0 to about 7.5. In one embodiment, the buffer has a pKa of 6.0. In one embodiment, the buffer has a pKa of 6.4. In one embodiment, the buffer has a pKa of 6.5. In one embodiment, the buffer has a pKa of 7.2.

In one embodiment, the buffer is a phosphate buffer. In one embodiment, the phosphate is at a concentration of 5 mM±0.75 mM to 50 mM±7.5 mM. In one embodiment, the phosphate is at a concentration of 5 mM±0.75 mM or about 5 mM. In one embodiment, the phosphate is at a concentration of 10 mM±1.5 mM or about 10 mM. In one embodiment, the phosphate is at a concentration of 15 mM±2.25 mM or about 15 mM. In one embodiment, the phosphate is at a concentration of 20 mM±3 mM or about 20 mM. In one embodiment, the phosphate is at a concentration of 25 mM±3.75 mM or about 25 mM. In one embodiment, the phosphate is at a concentration of 30 mM±4.5 mM or about 30 mM. In one embodiment, the phosphate is at a concentration of 35 mM±5.25 mM or about 35 mM. In one embodiment, the phosphate is at a concentration of 40 mM±6 mM or about 40 mM. In one embodiment, the phosphate is at a concentration of 45 mM±6.75 mM or about 45 mM. In one embodiment, the phosphate is at a concentration of 50 mM±7.5 mM or about 50 mM.

In one embodiment, the organic cosolvent is a nonionic polymer containing a polyoxyethylene moiety. In some embodiments, the organic cosolvent is any one or more of polysorbate 20, polysorbate 80, poloxamer 188, and polyethylene glycol 3350. In a specific embodiment, the organic cosolvent is polysorbate 20.

In one embodiment, the organic cosolvent is at a concentration of from about 0.005%±0.00075% to about 1%±0.15% "weight to volume" or "w/v", wherein, e.g., 0.1 g/ml=10% and 0.01 g/ml=1%. In one embodiment, the organic cosolvent is polysorbate 20, which is at a concentration of 0.2%±0.03% w/v, or about 0.2% w/v. In another embodiment, the organic cosolvent is polysorbate 20, which is at a concentration of 0.01%±0.0015% w/v or about 0.01% w/v.

In one embodiment, the stabilizer is a sugar, a salt, an amino acid, or a combination of any one or more thereof. In one embodiment, the sugar is selected from the group consisting of sucrose, sorbitol, mannitol, glycerol and trehalose; the salt is sodium chloride; and the amino acid is glycine. In one embodiment, the stabilizer comprises a combination of sucrose and sodium chloride.

In one embodiment, the sucrose is at a concentration of from about 5% to about 40%, w/v; and the sodium chloride is from about 50 mM to about 250 mM. In a specific embodiment, the formulation comprises 10%±1.5%, about 10%, or 10% sucrose; and 150 mM±22.5 mM, about 150 mM, or 150 mM sodium chloride. In another embodiment, the formulation comprises 20%±3%, about 20%, or 20% sucrose.

In one embodiment, the viscosity of the formulation is about 1 cPoise to about 5 cPoise. In one embodiment, the viscosity of the formulation is 1.5 cPoise±0.23 cPoise, about 1.5 cPoise, or 1.5 cPoise.

In one embodiment, the osmolality of the formulation is close to within a physiological range. In one embodiment, the formulation has an osmolality of about 300 milliOsmoles per kilogram (mOsm) to about 700 mOsm. In one embodiment, the osmolality of the formulation is 650 mOsm±98 mOsm, about 650 mOsm, or 650 mOsm.

In one embodiment, at least 95% of the anti-Dll4 antibody recovered from the liquid pharmaceutical formulation after 24 months of storage at −80° C. is non-aggregated and un-degraded, as determined by size exclusion chromatography. In one embodiment, at least 57% of the anti-Dll4 antibody recovered from the liquid pharmaceutical formulation after 24 months of storage at −80° C. is of the non-basic and non-acidic form (i.e., main peak or main charge form or "region 2 peak"), as determined by ion exchange chromatography. In one embodiment, anti-Dll4 on average maintains from about 65% to about 135% of its binding activity after 24 months of storage at −80° C., relative to the binding activity of the antibody prior to storage.

In one embodiment, at least 95% of the anti-Dll4 antibody recovered from the liquid pharmaceutical formulation after 18 months of storage at −30° C. is non-aggregated and un-degraded, as determined by size exclusion chromatography. In one embodiment, at least 57% of the anti-Dll4 antibody recovered from the liquid pharmaceutical formulation after 18 months of storage at −30° C. is of the main charge form, as determined by ion exchange chromatography. In one embodiment, the anti-Dll4 antibody maintains on average about 65% to about 135% of its binding activity after 18 months of storage at −30° C., relative to the binding activity of the antibody prior to storage.

In one embodiment, at least 95% of the anti-Dll4 antibody recovered from the liquid pharmaceutical formulation after six months of storage at −20° C. is non-aggregated and un-degraded, as determined by size exclusion chromatography. In one embodiment, at least 60% of the anti-Dll4 antibody recovered from the liquid pharmaceutical formulation after six months of storage at −20° C. is of the main charge form, as determined by ion exchange chromatography. In one embodiment, the anti-Dll4 antibody maintains on average about 65% to about 135% of its binding activity after six months of storage at −20° C., relative to the binding activity of the antibody prior to storage.

In one embodiment, at least 95% of the anti-Dll4 antibody recovered from the liquid pharmaceutical formulation after six months of storage at 5° C. is non-aggregated and un-degraded, as determined by size exclusion chromatography. In one embodiment, at least 61% of the anti-Dll4 antibody recovered from the liquid pharmaceutical formulation after six months of storage at 5° C. is of the main charge form, as determined by ion exchange chromatography. In one embodiment, the anti-Dll4 antibody maintains on average about 65% to about 135% of its binding activity after six months of storage at 5° C., relative to the binding activity of the antibody prior to storage.

In one embodiment, at least 97% of the anti-Dll4 antibody recovered from the liquid pharmaceutical formulation after six months of thermal stress at 25° C. is non-aggregated and un-degraded, as determined by size exclusion chromatography. In one embodiment, at least 53% of the anti-Dll4 antibody recovered from the liquid pharmaceutical formulation after six months of storage at 25° C. is of the main charge form, as determined by ion exchange chromatography. In one embodiment, the anti-Dll4 antibody maintains on average about 65% to about 135% of its binding activity after six months of storage at 25° C., relative to the binding activity of the antibody prior to storage.

In one embodiment, at least 94% of the anti-Dll4 antibody recovered from the liquid pharmaceutical formulation after 28 days of thermal stress at 45° C. is non-aggregated and un-degraded, as determined by size exclusion chromatography. In one embodiment, at least 45% of the anti-Dll4 antibody recovered from the liquid pharmaceutical formulation after 28 days of thermal stress at 45° C. is of the main charge form, as determined by ion exchange chromatography. In one embodiment, the anti-Dll4 antibody maintains on average about 65% to about 135% of its binding activity after 28 days of thermal stress at 45° C., relative to the binding activity of the antibody prior to application of the thermal stress condition.

In one embodiment, at least 96% of the anti-Dll4 antibody recovered from the liquid pharmaceutical formulation after 28 days of thermal stress at 37° C. is non-aggregated and un-degraded, as determined by size exclusion chromatography. In one embodiment, at least 51% of the anti-Dll4 antibody recovered from the liquid pharmaceutical formulation after 28 days of thermal stress at 37° C. is of the main charge form, as determined by ion exchange chromatography. In one embodiment, the anti-Dll4 antibody maintains on average about 65% to about 135% of its binding activity after 28 days of thermal stress at 37° C., relative to the binding activity of the antibody prior to application of the thermal stress condition.

In one embodiment, at least 97% of the anti-Dll4 antibody recovered from the liquid pharmaceutical formulation after 28 days of thermal stress at 25° C. is non-aggregated and un-degraded, as determined by size exclusion chromatography. In one embodiment, at least 57% of the anti-Dll4 antibody recovered from the liquid pharmaceutical formulation after 28 days of thermal stress at 25° C. is of the main charge form, as determined by ion exchange chromatography. In one embodiment, the anti-Dll4 antibody maintains on average about 65% to about 135% of its binding activity after 28 days of thermal stress at 25° C., relative to the binding activity of the antibody prior to application of the thermal stress condition.

In one embodiment, at least 98% of the anti-Dll4 antibody recovered from the liquid pharmaceutical formulation after 120 minutes of agitation stress is non-aggregated and un-degraded, as determined by size exclusion chromatography. In one embodiment, at least 59% of the anti-Dll4 antibody recovered from the liquid pharmaceutical formulation after 120 minutes of agitation stress is of the main charge form, as determined by ion exchange chromatography. In one embodiment, the anti-Dll4 maintains on average about 65% to about 135% of its binding activity after 120 minutes of agitation stress, relative to the binding activity of the antibody prior to application of the agitation stress condition.

In one embodiment, at least 98% of the anti-Dll4 antibody recovered from the liquid pharmaceutical formulation after eight freeze/thaw cycles is non-aggregated and un-degraded, as determined by size exclusion chromatography. In one embodiment, at least 58% of the anti-Dll4 antibody recovered from the liquid pharmaceutical formulation after eight freeze/thaw cycles is of the main charge form, as determined by ion exchange chromatography. In one embodiment, the anti-Dll4 maintains on average about 65% to about 135% of its binding activity after eight freeze/thaw cycles, relative to the binding activity of the antibody prior to application of the freeze/thaw stress condition.

In one aspect, a liquid pharmaceutical formulation is provided, comprising: (i) from 20±3 mg/ml to 75±11.25 mg/ml of a human antibody that specifically binds to human Dll4; (ii) from 5 mM±0.75 mM to 50 mM±7.5 mM phosphate; (iii) from 0.005%±0.000075% to 1%±0.15% (w/v) polysorbate 20; (iv) from 5%±0.75% to 40%±6% (w/v) sucrose; and (v) from 50 mM±7.5 mM to 250 mM±37.5 mM sodium chloride, at a pH of from about 5.5 to about 6.5. The anti-Dll4 antibody of this aspect comprises a heavy chain variable region (HCVR) and a light chain variable region (LCVR) such that the HCVR/LCVR combination comprises heavy and light chain complementarity determining regions (HCDR1-HCDR2-HCDR3/LCDR1-LCDR2-LCDR3), which comprise the amino acid sequences of SEQ ID NOs:2-3-4/SEQ ID NOs:6-7-8, respectively. In a particular embodiment, the anti-Dll4 antibody comprises a heavy chain variable region (HCVR) and light chain variable region (LCVR) comprising an amino acid sequence of SEQ ID NO: 1 and SEQ ID NO: 5, respectively (antibody REGN421 of U.S. Pat. Nos. 7,488,806, 7,534,868, and 7,919,593, and U.S. Pat. App. Pub. No. 2011-0150905, which are herein incorporated by reference in their entirety).

In one embodiment, the liquid formulation comprises (i) 25 mg/ml±3.75 mg/ml of antibody REGN421; (ii) 10±1.5 mM phosphate; (iii) 0.2%±0.03% (w/v) polysorbate 20; (iv) 10%±1.5% (w/v) sucrose; and (v) 150 mM±22.5 mM sodium chloride at a pH of 6.0±0.5. In one embodiment, after thermal stress of the formulation at 45° for 28 days, ≥94% of the antibody retains its native conformation, ≥45% of the antibody is of the main charge form, and ≥98% of the antibody retains its binding activity. In another embodiment, after thermal stress of the formulation at 37° for 28 days, ≥97% of the antibody is native and ≥59% of the antibody is of the main charge form, and about 100% of the antibody retains its binding activity. In one embodiment, after thermal stress of the formulation at 25° for 28 days, ≥97% of the antibody is native and ≥57% of the antibody is of the main charge form, and about 100% of the antibody retains its binding activity. In one embodiment of this particular formulation, after eight cycles of freezing followed by thawing, ≥98% of the antibody is native and ≥59% of the antibody is of the main charge form, and about 100% of the antibody retains its binding activity. In one embodiment of this particular formulation, after 120 minutes of agitation stress, ≥98% of the antibody is native and ≥58% of the antibody is of the main charge form, and at least about 98% of the antibody retains its potency.

In one aspect, a liquid pharmaceutical formulation of any of the preceding aspects is provided in a container. In one embodiment, the container is a polycarbonate vial. In another embodiment, the container is a glass vial, which in some embodiments is a type 1 borosilicate glass vial with a fluorocarbon-coated butyl rubber stopper. In yet another embodiment, the container is a bag, such as an intravenous drip (IV) bag, which in some embodiments is made of polyvinyl chloride or polyolefin. In another embodiment, the container is an injection device, such as a microinfuser or a syringe.

In one aspect, a pharmaceutical formulation comprising (a) 25 mg/mL±3.75 mg/mL of an anti-Ang-2 antibody, (b) 10 mM±1.5 mM phosphate, pH 6±0.5, (c) 0.2%±0.03% polysorbate 20, (d) 10% w/v±1.5% sucrose, and (e) 150 mM±22.5 mM sodium chloride is provided, wherein (a) the antibody comprises an HCVD of SEQ ID NO: 1 and an LCVD of SEQ ID NO: 5, (b) the antibody has a molecular mass of about 146 kDa, about 147 kDa, or about 150 kDa, (c) from about 82% to about 87% of the antibodies contain fucosylated oligosaccharide chains, and (d) the heavy chains of the antibody lack a C-terminal lysine.

In one embodiment, the pharmaceutical formulation consists of (a) 25 mg/mL±3.75 mg/mL of an anti-Ang-2 antibody, (b) 10 mM±1.5 mM phosphate, pH 6±0.5, (c) 0.2%±0.03% polysorbate 20, (d) 10%±1.5% sucrose, and (e) 150 mM±22.5 mM sodium chloride is provided, wherein (a) the antibody comprises an HCVD of SEQ ID NO: 1 and an LCVD of SEQ ID NO: 5, (b) the antibody has a molecular mass of about 146 kDa, about 147 kDa, or about 150 kDa, (c) from about 82% to about 87% of the antibodies contain fucosylated oligosaccharide chains, and (d) the heavy chains of the antibody lack a C-terminal lysine.

In one aspect, a kit comprising a pharmaceutical composition of any one of the preceding aspects, a container, and instructions is provided. In one embodiment, the container is a prefilled syringe. In one embodiment, the container is a borosilicate vial fitted with a FLUROTEC-coated 4023/50-rubber stopper.

Other embodiments of the present invention will become apparent from a review of the ensuing detailed description.

DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 5%. For example, as used herein, the expression "about 100" includes 95 and 105 and all values in between (e.g., 95.00, 95.01, 95.02, 95.03, 95.04, . . . , 104.96, 104.97, 104.98, 104.99, 105.00).

Although any methods and materials similar or equivalent to those described herein can be used in the practice or testing of the present invention, the preferred methods and materials are now described. All publications mentioned herein are incorporated herein by reference in their entirety.

Pharmaceutical Formulations

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human delta-like ligand-4 (Dll4) protein. More specifically, the present invention includes pharmaceutical formulations that comprise: (i) a human antibody that specifically binds to human Dll4 (ii) a phosphate buffer; (iii) an organic cosolvent that is a non-ionic surfactant; and (iv) a stabilizer that is a carbohydrate or an inorganic salt, or a combination of carbohydrate and inorganic salt. Specific exemplary components and formulations included within the present invention are described in detail below.

Antibodies that Bind Specifically to Dll4

The pharmaceutical formulations of the present invention may comprise a human antibody, or an antigen-binding fragment thereof, that binds specifically to human Dll4. As used herein, the term "Dll4" means a human delta-like ligand 4, which is a vascular-specific ligand of Notch. The Dll4-Notch signaling pathway is generally understood to modulate angiogenesis by blocking blood vessel branching and promoting blood vessel maturation (Dll4 as a negative regulator of branching; reviewed in Sainsin and Harris, *Trends in Molecular Medicine*, Vol. 13(9):389-395, September 2007.) Agents that antagonize the Dll4-Notch pathway have been shown to inhibit the rate of tumor growth by "triggering excessive but nonfunctional angiogenesis." (See Sainsin at 389.) Dll4 is upregulated by VEGF and is thought to promote the organized development of functional neo-vessels. An exemplary human Dll4 amino acid sequence is described in SEQ ID NO: 9. Antibodies to human Dll4 are described in U.S. Pat. Nos. 7,488,806, 7,534,868, and 7,919,593, which are herein incorporated by reference.

The term "antibody", as used herein, is generally intended to refer to immunoglobulin molecules comprising four polypeptide chains: two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementary determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody", as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to human Dll4 or an epitope thereof.

An "isolated antibody", as used herein, is intended to refer to an antibody that is substantially free of other antibodies having different antigenic specificities (e.g., an isolated antibody that specifically binds human Dll4 is substantially free of antibodies that specifically bind antigens other than human Dll4), with the notable exception of bi-specific (or multi-specific) antibodies that specifically bind Dll4 on the one hand, and another epitope on the other. Moreover, an isolated antibody may be substantially free of other cellular material or chemicals.

The term "specifically binds", or the like, means that an antibody or antigen-binding fragment thereof forms a complex with an antigen that is relatively stable under physiologic conditions. Specific binding can be characterized by a dissociation constant of at least about $1 \times 10^{-6}$ M or greater. Methods for determining whether two molecules specifically bind are well known in the art and include, for example, equilibrium dialysis, surface plasmon resonance, and the like. An isolated antibody that specifically binds human Dll4 may, however, have cross-reactivity to other antigens, such as Dll4 molecules from other species (orthologs). In the context of the present invention, multispecific (e.g., bispecific) antibodies that bind to human Dll4 as well as one or more additional antigens are deemed to "specifically bind" human Dll4.

Exemplary anti-human Dll4 antibodies that may be included in the pharmaceutical formulations of the present invention are set forth in U.S. Pat. Nos. 7,488,806, 7,534,868, 7,919,593, and U.S. Patent Application No. 2011-0150905, the disclosures of which are incorporated herein by reference in their entirety.

According to certain embodiments of the present invention, the anti-human Dll4 antibody is a human IgG1 comprising a heavy chain variable region of the IGHV3-33.01 subtype and a light chain variable region of the IGKV3-11.01 subtype (see Barbie and Lefranc, The Human Immunoglobulin Kappa Variable (IGKV) Genes and Joining (IGKJ) Segments, Exp. Clin. Immunogenet. 1998; 15:171-

183; and Scaviner, D. et al., Protein Displays of the Human Immunoglobulin Heavy, Kappa and Lambda Variable and Joining Regions, Exp. Clin. Immunogenet., 1999; 16:234-240). The germline IGHV3-33 and IGKV3-11 sequences, and the amino acid position assignment numbers presented herein comport with the international Immunogenetics (IMGT) information system, as described in Lefranc, M.-P., et al., IMGT®, the international ImMunoGeneTics information System®, Nucl. Acids Res, 37, D1006-D1012 (2009).

In some embodiments, the anti-human Dll4 antibody comprises one or more amino acid substitutions in one or more framework regions relative to the canonical heavy chain variable region, which is reasonably expected to result in an altered charge distribution across the exposed surface of the antibody, and therefore affect its interaction with the surrounding solvent and excipients. In some embodiments, the amino acid substitution comprises a substitution of serine foralanine, methionine for threonine, and/or glutamic acid for glutamine at IMGT positions 54, 86, and 90, respectively, of IGHV3-33.

In some embodiments, the anti-human Dll4 antibody comprises one or more amino acid substitutions in one or more CDRs relative to the canonical light chain variable region, which is reasonably expected to result in an altered charge distribution across the exposed surface of the antibody, and therefore affect its interaction with the solvent environment. In some embodiments, the amino acid substitution comprises the substitution of histidine for glutamine at IMGT position 106 of IGKV3-11.

According to certain embodiments of the present invention, the anti-human Dll4 antibody, or antigen-binding fragment thereof, comprises a heavy chain complementary determining region (HCDR) 1 of SEQ ID NO: 2, an HCDR2 of SEQ ID NO: 3, and an HCDR3 of SEQ ID NO: 4. In certain embodiments, the anti-human Dll4 antibody, or antigen-binding fragment thereof, comprises an HCVD of SEQ ID NO: 1.

According to certain embodiments of the present invention, the anti-human Dll4, or antigen-binding fragment thereof, comprises a light (kappa) chain complementary determining region (LCDR) 1 of SEQ ID NO: 6, an LCDR2 of SEQ ID NO: 7, and an LCDR3 of SEQ ID NO: 8. In certain embodiments, the anti-human Dll4 antibody, or antigen-binding fragment thereof, comprises an LCVD of SEQ ID NO: 5.

The non-limiting, exemplary antibody used in the Examples herein is referred to as REGN421, as in U.S. Pat. No. 7,488,806, U.S. Pat. No. 7,534,868, U.S. Pat. No. 7,919,593, and US 2011-0150905. This antibody comprises an HCVR/LCVR amino acid sequence pair having SEQ ID NOs: 1/5, and HCDR1-HCDR2-HCDR3/LCDR1-LCDR2-LCDR3 domains represented by SEQ ID NOs: 2-3-4/SEQ ID NOs: 6-7-8.

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 20 mg/mL±3 mg/mL to 75 mg/mL±11.25 mg/mL of antibody; 25±3.75 mg/mL to 70±10.5 mg/mL of antibody; 30±4.5 mg/mL to 65±9.75 mg/mL of antibody; 35±5.25 mg/mL to 60±9 mg/mL of antibody; 40±6 mg/mL to 55±8.25 mg/mL of antibody; 45±6.75 mg/mL to 50±7.5 mg/mL of antibody; 25 mg/mL±3.75 mg/mL; about 25 mg/mL; 25 mg/mL; 50 mg/mL±7.5 mg/mL; about 50 mg/mL; or 50 mg/mL of an antibody or an antigen-binding fragment thereof, that binds specifically to human Dll4.

Excipients and pH

The pharmaceutical formulations of the present invention comprise one or more excipients. The term "excipient", as used herein, means any non-therapeutic agent added to the formulation to provide a desired consistency, viscosity or stabilizing effect.

In certain embodiments, the pharmaceutical formulation of the invention comprises at least one organic cosolvent in a type and in an amount that stabilizes the human Dll4 antibody under conditions of rough handling or agitation, such as, e.g., vortexing. In some embodiments, what is meant by "stabilizes" is the maintenance of at least 95% of the Dll4 antibody in its native state, i.e., not fragmented or aggregated, of antibody (on a molar basis) over the course of rough handling, such as by vortexing the antibody-organic cosolvent solution for about 60 minutes or about 120 minutes.

In certain embodiments, the organic cosolvent is a non-ionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 188 is also known as PLURONIC F68.

The amount of non-ionic surfactant contained within the pharmaceutical formulations of the present invention may vary depending on the specific properties desired of the formulations, as well as the particular circumstances and purposes for which the formulations are intended. In certain embodiments, the formulations may contain 0.01%±0.0015% to 1%±0.15% surfactant. For example, the formulations of the present invention may comprise about 0.0085%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.3%; about 0.4%; about 0.5%; about 0.6%; about 0.7%; about 0.8%; about 0.9%; about 1%; about 1.1%; about 1.15%; or about 1.2% polysorbate 20 or poloxamer 188.

The pharmaceutical formulations of the present invention may also comprise one or more stabilizers in a type and in an amount that stabilizes the human Dll4 antibody under conditions of thermal stress. In some embodiments, what is meant by "stabilizes" is maintaining greater than about 94% of the antibody in a native conformation when the solution containing the antibody and the thermal stabilizer is kept at about 45° C. for up to about 28 days. In some embodiments, what is meant by "stabilizes" is maintaining greater than about 96% of the antibody in a native conformation when the solution containing the antibody and the thermal stabilizer is kept at about 37° C. for up to about 28 days. As used herein, "native" means the major form of the antibody by size exclusion, which is generally an intact monomer of the antibody.

In certain embodiments, the thermal stabilizer is a sugar or sugar alcohol selected from sucrose, sorbitol, glycerol, trehalose and mannitol, or any combination thereof, the amount of which contained within the formulation can vary depending on the specific circumstances and intended purposes for which the formulation is used. In certain embodiments, the formulations may contain about 5% to about 40% sugar or sugar alcohol; about 1% to about 20% sugar or sugar alcohol; about 5% to about 15% sugar or sugar alcohol; about 7.5% to about 12.5% sugar or sugar alcohol; about 10% sugar or sugar alcohol; 10%±1.5% sugar or sugar alcohol; or 10% sugar or sugar alcohol. For example, the pharmaceutical formulations of the present invention may comprise 4%±0.6%; 5%±0.75%; 6%±0.9%; 7%±1.05%; 8%±1.2%; 9%±1.35%; 10%±1.5%; 11%±1.65%; 12%±1.8%; 13%±1.95%; or about 14%±2.1% sugar or sugar alcohol (e.g., sucrose, trehalose or mannitol).

The pharmaceutical formulations of the present invention may also comprise a buffer or buffer system, which serves to maintain a stable pH and to help stabilize the human Dll4 antibody. In some embodiments, what is meant by "stabilizes" is wherein at least 94% of the antibody is in its native conformation as determined by size exclusion chromatography when the solution containing the antibody and the buffer is kept at about 45° C. for up to about 28 days. By "native" or "native conformation", what is meant is the antibody fraction that is not aggregated or degraded. This is generally determined by an assay that measures the relative size of the antibody entity, such as a size exclusion chromatographic assay. The non-aggregated and non-fragmented antibody elutes at a fraction that equates to the native antibody, and is generally the main elution fraction. Aggregated antibody elutes at a fraction that indicates a size greater than the native antibody. Fragmented antibody elutes at a fraction that indicates a size less than the native antibody.

In some embodiments, what is meant by "stabilizes" is wherein at least 45% of the antibody is in its main charge form as determined by cation exchange chromatography when the solution containing the antibody and the buffer is kept at about 45° C. for up to about 28 days. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present invention may have a pH of from about 5.5 to about 6.5. For example, the formulations of the present invention may have a pH of about 5.5; about 5.6; about 5.7; about 5.8; about 5.9; about 6.0; about 6.1; about 6.2; about 6.3; about 6.4; or about 6.5. In some embodiments, the pH is 6.0±0.5; 6.0±0.4; 6.0±0.3; 6.0±0.2; 6.0±0.1; about 6.0; or 6.0.

In some embodiments, the buffer or buffer system comprises at least one buffer that has a buffering range that overlaps fully or in part the range of pH 5.5-7.4, such as, e.g., a buffer having a useful buffering range of pH 4.8 to pH 8.8. In one embodiment, the buffer has a pKa of about 7.21. In certain embodiments, the buffer comprises a phosphate buffer. In certain embodiments, the phosphate is present at a concentration of 5 mM±0.75 mM to 15 mM±2.25 mM; 6 mM±0.9 mM to 14 mM±2.1 mM; 7 mM±1.05 mM to 13 mM±1.95 mM; 8 mM±1.2 mM to 12 mM±1.8 mM; 9 mM±1.35 mM to 11 mM±1.65 mM; 10 mM±1.5 mM; or about 10 mM. In certain embodiments, the buffer system comprises phosphate at 10 mM±1.5 mM, at a pH of 6.0±0.5.

Exemplary Formulations

According to one aspect of the present invention, the liquid pharmaceutical formulation has low viscosity (i.e, less than 10 cPoise, or about 1.5 cPoise) and has an osmolality between 600 and 700 mOsm, or about 650 mOsm; and comprises: (i) 25 mg/mL±3.75 mg/mL, or 50 mg/mL±7.5 mg/mL of a human antibody that specifically binds to human Dll4 (e.g., REGN421); (ii) a buffer system that buffers at about pH 6.0±0.5; (iii) a thermal stabilizer comprising a sugar and a salt, which serves as a; and (iv) an organic cosolvent.

According to one embodiment, the pharmaceutical formulation comprises: (i) 20±3 mg/mL to 60±9 mg/mL human IgG1 antibody that specifically binds to human Dll4 and which comprises a substituted IGHV3-33 type heavy chain variable region and a substituted IGKV3-11 type light chain variable region; (ii) a phosphate buffer, which buffers at pH 6.0±0.5; (iii) sucrose and sodium chloride; and (iv) a non-ionic detergent, such as a polysorbate.

According to one embodiment, the pharmaceutical formulation comprises: (i) 25 mg/ml±3.75 mg/mL human IgG1 antibody that specifically binds to human Dll4, and which comprises an HCDR1 of SEQ ID NO: 2, an HCDR2 of SEQ ID NO: 3, an HCDR3 of SEQ ID NO: 4, an LCDR1 of SEQ ID NO: 6, an LCDR2 of SEQ ID NO: 7, and an LCDR3 of SEQ ID NO: 8; (ii) 10 mM±1.5 mM phosphate, pH 6.0±0.5; (iii) 10%±1.5% sucrose; (iv) 150 mM±22.5 mM sodium chloride; and (v) 0.2%±0.03% polysorbate 20.

According to one embodiment, the pharmaceutical formulation comprises: (i) 50 mg/ml±7.5 mg/mL human IgG1 antibody that specifically binds to human Dll4, and which comprises an HCDR1 of SEQ ID NO: 2, an HCDR2 of SEQ ID NO: 3, an HCDR3 of SEQ ID NO: 4, an LCDR1 of SEQ ID NO: 6, an LCDR2 of SEQ ID NO: 7, and an LCDR3 of SEQ ID NO: 8; (ii) 10 mM±1.5 mM phosphate, pH 6.0±0.5; (iii) 10%±1.5% sucrose; (iv) 150 mM±22.5 mM sodium chloride; and (v) 0.2%±0.03% polysorbate 20.

According to one embodiment, the pharmaceutical formulation comprises: (i) 25 mg/ml±3.75 mg/mL human IgG1 antibody that specifically binds to human Dll4, and which comprises a heavy chain variable domain of SEQ ID NO: 1, and a light chain variable domain of SEQ ID NO: 5, at a concentration of; (ii) 10 mM±1.5 mM phosphate pH 6.0±0.5; (iii) 10%±1.5% sucrose; (iv) 150 mM±22.5 mM sodium chloride; and (iv) 0.2%±0.03% polysorbate 20.

According to one embodiment, the pharmaceutical formulation comprises: (i) 50 mg/ml±7.5 mg/mL human IgG1 antibody that specifically binds to human Dll4, and which comprises a heavy chain variable domain of SEQ ID NO: 1, and a light chain variable domain of SEQ ID NO: 5; (ii) 10 mM±1.5 mM phosphate, pH 6.0±0.5; (iii) 10%±1.5% sucrose; (iv) 150 mM±22.5 mM sodium chloride; and (v) 0.2%±0.03% polysorbate 20.

Additional non-limiting examples of pharmaceutical formulations encompassed by the present invention are set forth elsewhere herein, including the working Examples presented below.

Stability and Viscosity of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of at least about 90%, 95%, 96%, 97%, 98% or 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion high performance liquid chromatography [SE-HPLC]), such that native means non-aggregated and non-fragmented. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C. Thermal stress may be applied to the pharmaceutical formulation to assess stability. Thermal stress includes for example holding the formulation for about 14 days or about 28 days at about 25° C., about 35° C., about 37° C., or about 45° C.

For example, a pharmaceutical formulation may be deemed stable if after six months of storage at 5° C., at least 90%, 91%, 92%, 93%, 94%, 95%, 96%, 97%, 98%, 98.5%, 99% or 99.5% of antibody detected by SE-HPLC is native (i.e., in the native peak fraction). A pharmaceutical formulation may also be deemed stable if after six months of storage at 25° C. at least 97%, 97.5%, 98%, 98.5%, 99% or 99.5% of antibody detected by SE-HPLC is native. A pharmaceutical formulation may also be deemed stable if after 28 days of storage at 37° C., at least 96%, 96.5%, 97%, 97.5%, 98%, 98.5%, 99% or 99.5% of antibody detected by SE-HPLC is native. A pharmaceutical formulation may also be deemed stable if after 28 days of storage at 45° C. at least 94%, 95%, 96%, 97%, 98% or 99% of antibody detected by SE-HPLC is native. A pharmaceutical formulation may also be deemed stable if after six months of storage at −20° C. at least 98.5%, 99% or 99.5% of antibody detected by SE-HPLC is native. A pharmaceutical formulation may also be deemed stable if after 18 months of storage at −30° C. at least 99% or 99.5% of antibody detected by SE-HPLC is native. A pharmaceutical formulation may also be deemed stable if after six months of storage at −80° C. at least 99% or 99.5% of antibody detected by SE-HPLC is native.

Stability can be measured, inter alia, by determining the percentage of antibody that migrates in the main fraction of antibody ("main charge form") during ion exchange, relative to the total combined peak area, wherein stability is proportional to the fraction of antibody in the main charge form. While not wishing to be bound by theory, deamidation of the antibody may cause the antibody to become more negatively charged and thus more acidic relative to the non-deamidated antibody (see, e.g., Robinson, N., Protein Deamidation, PNAS, Apr. 16, 2002, 99(8):5283-5288). An "acceptable degree of stability", as that phrase is used herein, means that at least 53% of the antibody is in a main charge form detected in the formulation after storage for a defined amount of time at a defined temperature. In certain embodiments an acceptable degree of stability means that at least about 53%, 54%, 55%, 56%, 57%, 58%, 59%, 60%, 61%, 62%, 65%, 70%, 75%, 80%, 85%, 90%, 95%, or 99% of the antibody can be detected in a main charge form after storage for a defined amount of time at a given temperature, or under thermal, freeze/thaw, or agitation stress. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 37° C., or about 45° C. For example, a pharmaceutical formulation may be deemed stable if after three months of storage at −80° C., −30° C., or −20° C. no less than about 57%, 58%, 59%, 60%, or 61% of the antibody is in a main charge form. A pharmaceutical formulation may also be deemed stable if after six months of storage at 5° C., no less than about 59%, 59.1%, 59.2%, 59.3%, 59.4%, 59.5%, 59.6%, 59.7%, 59.8%, 59.9%, 60%, 60.1%, 60.2%, 60.3%, 60.4%, 60.5%, 60.6%, 60.7%, 60.8%, 60.9%, 61%, or 61.1% of the antibody is in a main charge form. A pharmaceutical formulation may also be deemed stable if after six months of storage at 25° C., no less than about 53% of the antibody is in a main charge form. A pharmaceutical formulation may also be deemed stable if after 28 days of storage at 37° C., no less than about 50%, 50.5%, 51%, or 51.5% of the antibody is in a main charge form. A pharmaceutical formulation may also be deemed stable if after 28 days of storage at 45° C., no less than about 45%, 45.1%, 45.2%, 45.3%, 45.4%, 45.5%, 45.6%, 45.7%, 45.8%, 45.9%, or 50% of the antibody can be detected in a main charge form.

Measuring the binding affinity of the antibody to its target may also be used to assess stability. For example, a formulation of the present invention may be regarded as stable if, after storage at e.g., −80° C., −30° C., −20° C., 5° C., 25° C., 37° C., 45° C., etc. for a defined amount of time (e.g., 14 days to 24 months), the anti-Dll4 antibody contained within the formulation maintains at least 50% and up to about 150% of the potency, as measured as binding affinity, of the antibody prior to said storage. Binding affinity may be determined by e.g., ELISA or plasmon resonance. Biological activity may be determined by a Dll4 activity assay, such as e.g., by contacting a cell that expresses Dll4 with the formulation comprising the anti Dll4 antibody. The binding of the antibody to such a cell may be measured directly, such as via FACS analysis. Alternatively, the downstream activity of the Dll4/Notch signalling pathway may be measured in the presence of the antibody, and compared to the activity of the Dll4/Notch signaling pathway in the absence of antibody. In some embodiments, the Dll4 may be endogenous to the cell. In other embodiments, the Dll4 may be ectopically (heterologously) expressed in the cell.

Additional methods for assessing the stability of an antibody in formulation are demonstrated in the Examples presented below.

Containers and Methods of Administration

The pharmaceutical formulations of the present invention may be contained within any container suitable for storage or administration of medicines and other therapeutic compositions. For example, the pharmaceutical formulations may be contained within a sealed and sterilized plastic or glass container having a defined volume such as a vial, ampule, syringe, cartridge, bottle, or IV bag. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluoroTec®", available from West Pharmaceutical Services, Inc. (Lionville, Pa.). FluoroTec® is an example of a fluorocarbon coating used to minimize or prevent drug product from adhering to the rubber surfaces.

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park, Ill.).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. No. 6,629,949; U.S. Pat. No. 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In one embodiment, the pharmaceutical formulation is administered via an IV drip, such that the formulation is diluted in an IV bag containing a physiologically acceptable solution. In one embodiment, the pharmaceutical composition is a compounded sterile preparation in an intravenous infusion bag, such that a single dose of drug product is diluted into 100 mL, 250 mL (or other like amount suitable for intravenous drip delivery) of a physiological buffer (e.g., 0.9% saline). In some embodiments, the infusion bag is made of a polyvinyl chloride (e.g., VIAFLEX, Baxter, Deerfield, Ill.). In some embodiments, the infusion bag is made of a polyolefin (EXCEL IV Bags, Braun Medical Inc., Bethlehem, Pa.).

Therapeutic Uses of the Pharmaceutical Formulations

The pharmaceutical formulations of the present invention are useful, inter alia, for the treatment, prevention or amelioration of any disease or disorder associated with Dll4 activity, including diseases or disorders mediated by Dll4 or the Notch signaling pathway. Exemplary, non-limiting diseases and disorders that can be treated or prevented by the administration of the pharmaceutical formulations of the present invention include various diseases involving angiogenesis, which is the biological process whereby new blood vessels are formed. Aberrant angiogenesis is associated with several disease conditions including, e.g., proliferative retinopathies, rheumatoid arthritis and psoriasis. In addition, it is well established that angiogenesis is critical for tumor growth and maintenance.

EXAMPLES

The following examples are presented so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, percent concentration (%) means the mass of the solute in grams divided by the volume of the solution in milliliters times 100% (e.g., 10% sucrose means 0.1 gram of sucrose per milliliter of solution), temperature is in degrees Centigrade, and pressure is at or near atmospheric pressure.

Initial formulation development activities involved screening organic cosolvents, thermal stabilizers, and buffers in liquid and lyophilized formulations of anti-Dll4 antibodies to identify excipients that are compatible with the protein and enhance its stability, while maintaining near physiologic osmolality and low viscosity for intravenous and subcutaneous injection. Buffer conditions were also examined to determine the optimal pH for maximum protein stability.

Example 1: Exemplary Anti-Dll4 Formulation

Formulation development activities included the screening of buffers, organic cosolvents, and thermal stabilizers in liquid formulations of the anti-Dll4 antibody to identify excipients that enhance the stability of the protein. Buffer conditions were also examined to determine the optimal pH for maximum protein stability. Results generated from these studies were used to develop a stable, liquid formulation suitable for clinical use. Anti-Dll4 (e.g., REGN421) was formulated at 25±3.75 mg/ml or 50±7.5 mg/ml. In one embodiment, the anti-Dl14 antibody is formulated in 10±1.5 mM phosphate (pH 6.0±0.5), 0.2%±0.03% polysorbate 20, 10%±1.5% sucrose, and 150 mM±22.5 mM sodium chloride. The phosphate buffer, which is a combination of monobasic phosphate and dibasic phosphate, was selected for its buffering capacity at the optimal pH for anti-Dll4 stability and low rate of aggregation. Anti-Dll4 antibody REGN421 was observed to have optimum stability and the lowest rate of aggregation and formation of charge variants at pH 6.0. Polysorbate 20 was selected as the agitation stabilizing agent, which reduced the rate of aggregation and precipitation when the antibody was agitated and otherwise handled. Sucrose, which was observed to reduce the rate of aggregation of the antibody in solution, was selected as a component of the thermal stabilizing agent. Sodium chloride, which was observed to reduce the formation of charged species of the antibody in solution, was selected as another component of the thermal stabilizing agent.

Example 2: Stress Stability Study Methodology

Optical density (405 nm) and reverse-phase high-performance liquid chromatography (RP-HPLC) were used in development studies to assess the physical stability of the formulated anti-Dll4 antibody. Physical stability is defined as the recovery of soluble forms of the antibody in solution. Loss of antibody could be due to either precipitation or adsorption. The presence of particulates can be detected by visual inspection or by optical density (OD) measurements at 405 nm (turbidity measurements), where an increase in OD indicates an increase in turbidity due to the formation of particulates. The presence of particulates as determined visually or by OD measurements indicates that the sample has failed to maintain stability. Recovery of anti-Dll4 antibody was measured either by RP-HPLC and by UV spectrophotometry at 280 nm. The concentration of each test sample is determined from the area of the eluted antibody peak compared to a standard curve generated using antibody of defined concentration.

Size exclusion-HPLC (SE-HPLC) was used to assess the purity of the anti-Dll4 antibody and to provide a measure of the relative amounts of antibody aggregates, fragments and impurities that differ in molecular size from the subject anti-Dll4 antibody. Purified anti-Dll4 antibody generally eluted as a small aggregate peak and a large native dimer peak followed by a small low molecular weight peak. This method employed a high-resolution silica-based size exclusion column and a phosphate—sodium chloride buffer. Absorbance at 215 nm was recorded and integrated for purity determination. The purity specification for the anti-Dll4 antibody by SE-HPLC required that the area of the main peak was ≥90.0% of the total peak area. The percentages of the total peak area for the high and low molecular weight peaks areas are reported in the Tables.

Antibody charge variants were analyzed by cation exchange chromatography using a weak cation exchange column from Dionex (PROPAC® WCX-10, 4×250 mm) over a shallow salt gradient in phosphate buffer at pH 6.0 (40 mM to 120 mM NaCl over 44 minutes at 1 mL/min). Absorbance at 215 nm was recorded and integrated to assess charge heterogeneity. Chromatograms of anti-Dll4 antibody were integrated by dividing the peaks into three major charge groups: acidic, main and basic. The group of peaks that eluted first have been designated as the acidic species (this was determined by analyzing material exposed to high pH and temperature). The major peak in the chromatogram has been designated as the main peak, main charge form, or major charge variant. The final group of peaks was reported as the basic species. The designation was made based on the extended column retention most likely due to the high level of positive charge. The peak pattern of the antibody test sample was compared to the peak pattern of the reference standard and percent peak areas of the acidic, main and basic species were reported.

The activity or potency of the anti-Dll4 antibody was assessed using a binding assay. The ability of that antibody to block the binding of biotinylated-hDll4-hFc to Notch1 was measured using a specific and sensitive ELISA. The ELISA measured unbound biotinylated hDll4-hFc in a solution composed of a mixture of biotin-hDll4-hFc and anti-Dll4 antibody. The mixtures were added to microtiter plates coated with human Notch1. A fixed amount of biotin-hDll4-hFc was titrated with various amounts of antibody; and the antibody:biotin hDLL4 hFc complex was washed off. The amount of biotin-hDll4-hFc remaining bound to the plate was detected using Streptavidin conjugated to horseradish peroxidase (HRP). The analyzed samples were compared to a reference standard to determine relative potency. HRP colorimetric substrates were used for detection and OD450 nm was measured. The OD450 nm values were plotted against the concentrations of antibody in the solutions and an $IC_{50}$ was determined using non-linear regression analysis. The $IC_{50}$ was defined as the antibody concentration required to block 50% of the maximal binding of biotin-hDLL4-hFc to hNotch1-hFc coated plates, and these values reflect the blocking potency of the antibody against hDLL4. The potency was determined by comparison to a reference standard sample run on the same plate and expressed as a percent of the reference standard $IC_{50}$ value.

Example 3: Buffer and pH

The effect of pH and buffer on the stability of anti-Dll4 was considered. REGN421 antibody ("REGN421") was the most stable when formulated with either a 10 mM phosphate buffer or a 10 mM histidine buffer. Phosphate was chosen as the buffer for formulation due to concerns over the potential risk of histidine oxidation during storage in a liquid state.

RP-HPLC=Reverse phase high performance liquid chromatography; SE-HPLC=Size exclusion high performance liquid chromatography; CEX-HPLC=cation exchange high performance liquid chromatography.

TABLE 1

Effect of Buffer and pH on the Stability of REGN421 Incubated at 45° C. for 28 Days

| Buffer and pH | Visual Appearance | Turbidity (OD 405 nm) | % Total REGN421 Recovered (RP-HPLC) | % Native REGN421 Recovered (SE-HPLC) | % Native REGN421 Recovered (CEX-HPLC) |
|---|---|---|---|---|---|
| Starting Material* (no 45° C. incubation) | Pass | 0.00 | 100 | 97.6 | 58.5 |
| pH 8.0, Tris | Fail | 0.30 | 107 | 85.6 | 21.0 |
| pH 8.0, Phosphate | Fail | 0.27 | 100 | 65.7 | 5.6 |
| pH 7.5, Phosphate | Fail | 0.12 | 104 | 80.1 | 14.6 |
| pH 7.0, Phosphate | Fail | 0.03 | 104 | 83.4 | 24.9 |
| pH 6.5, Phosphate | Pass | 0.00 | 100 | 93.1 | 35.3 |
| pH 6.0, Phosphate | Pass | 0.00 | 104 | 93.9 | 38.3 |
| pH 6.0, Histidine | Pass | 0.00 | 103 | 94.4 | 41.6 |
| pH 6.0, Succinate | Pass | 0.01 | 102 | 92.3 | 40.7 |
| pH 6.0, Citrate | Pass | 0.01 | 99 | 92.4 | 36.7 |
| pH 5.5, Citrate | Fail | 0.01 | 105 | 91.1 | 34.6 |
| pH 5.0, Citrate | Fail | 0.02 | 103 | 86.7 | 26.9 |
| pH 5.0, Acetate | Pass | 0.01 | 107 | 92.3 | 34.6 |

The mixture of monobasic phosphate and dibasic phosphate results in a pH of 6.0 when all excipients are added together with the REGN421 antibody.

Analysis of buffered REGN421 incubated at elevated temperatures revealed that the main protein degradation pathways were the formation of aggregates, cleavage products, and charge variants. Therefore, to assess the effect of pH and buffer on REGN421 stability, REGN421 test samples were incubated at 45° C. in various buffers at pH values ranging from 5.0 to 8.0 to identify conditions that increase the thermal stability of the protein (Table 1). REGN421 had maximum stability, as determined by both SE-HPLC and Cation Exchange-High Performance Liquid Chromatography (CEX-HPLC) analysis, when the protein was formulated at pH 6.0. Formulating REGN421 in phosphate or histidine buffer at pH 6.0 resulted in greater protein stability compared to formulating at pH 6.0 in succinate or citrate buffer. Phosphate was chosen for the REGN421 formulation because of concerns over the potential risk of histidine oxidation during long term storage in a liquid state.

For the results shown in Table 1, 0.3 mL of 25 mg/mL REGN421 in 10 mM test buffer containing 0.2% polysorbate 20 in a 2 mL Type 1 borosilicate glass vial with a Fluoro-Tec® coated 4432/50 butyl rubber stopper were tested for 28 days at 45. Turbidity was reported as the change in $OD_{405}$ relative compared to starting material. Starting material results represent the average results of the starting material for all 14 formulations. OD=Optical density;

Example 4: Selection of Protectants Against Agitation Stress 0.2% polysorbate 20 was chosen as the organic cosolvent because it stabilized REGN421 when agitated in the liquid state. Studies that were initially performed to monitor the stability of REGN421 following agitation in the absence of organic cosolvents yielded varying results. Analysis of agitated REGN421 via SE-HPLC demonstrated an increase in aggregation of the antibody in one particular study, but no significant increase in aggregation was observed in the majority of other agitation studies performed on REGN421. Results from two representative stability studies are shown in Table 2. The conservative approach of adding polysorbate 20 to the REGN421 formulation was nonetheless taken to prevent potential agitation dependent protein instability that may occur during the manufacture, shipping, and handling of REGN421. Polysorbate 20 was chosen over other organic cosolvents because it did not change the thermal stability of REGN421.

For the antibody stability results shown in Table 2, 0.3 mL of 25 mg/mL REGN421, in 10 mM phosphate, pH 6.0 in a 2 mL Type 1 borosilicate glass vial with a FluoroTec® coated 4432/50 butyl rubber stopper was combined with the organic cosolvents and subjected to 120 minutes of vortexing. Turbidity was reported as the change in $OD_{405}$ relative compared to starting material. Starting material results represent the average results of the starting material for all nine formulations. OD=Optical density; RP-HPLC=Reverse phase high performance liquid chromatography; SE-HPLC=Size exclusion high performance liquid chromatography.

TABLE 2

Effect of Organic Cosolvents on Antibody Stability - Agitation

| Organic Cosolvent | Stress | Visual Appearance | % Total REGN421 Recovered (RP-HPLC) | % Native REGN421 Recovered (SE-HPLC) | % REGN421 Aggregate Recovered (SE-HPLC) |
|---|---|---|---|---|---|
| Starting Material* | None | Pass | 100 | 96.6 | 1.5 |
| No Cosolvent | Vortex 120 min | Pass | 101 | 94.9 | 3.0 |
| Starting Material* | None | Pass | 100 | 97.8 | 0.7 |
| No Cosolvent | Vortex 120 min | Pass | 101 | 97.4 | 0.9 |
| 0.2% Polysorbate 20 | Vortex 120 min | Pass | 99 | 98.0 | 0.7 |
| 0.2% Polysorbate 80 | Vortex 120 min | Pass | 100 | 97.9 | 0.8 |
| 0.2% PEG 3350 | Vortex 120 min | Pass | 101 | 98.0 | 0.7 |

Example 5: Selection of Protectants Against Thermal Stress

Stabilizers such as sugars, amino acids, and inorganic salts were examined for their ability to increase the thermal stability of REGN421. A summary of the thermal stabilizers that were examined is presented in Table 3. Formulations containing sucrose and trehalose showed the least amount of REGN421 aggregate formation as determined by SE-HPLC analysis. The addition of sodium chloride to the formulation was shown to decrease the formation of charge variants (CEX-HPLC) but resulted in an increased amount of aggregate formation (SE-HPLC). A subsequent study was conducted to examine the thermal stability of REGN421 following formulation with a combination of 10% sucrose and 150 mM sodium chloride (NaCl). The goal of this study was to reduce NaCl-induced aggregation by including sucrose in the formulation, thereby maintaining the protective effects of NaCl on charge variant formation within the formulation. The sucrose concentration was modulated from 20% (no NaCl) to 10% (with NaCl) to control the osmolality of the formulation. The thermal stability of REGN421 in this formulation as determined by CEX-HPLC analysis (formation of charge variants) was similar to results using NaCl as a single stabilizing agent (Table 3), demonstrating the protective effect of NaCl on charge variant formation. Furthermore, the rate of aggregate formation was significantly decreased compared to the formulation using NaCl as a single stabilizing agent, demonstrating the stabilizing effects of sucrose on the formulation. Based on these results, REGN421 was formulated with 10% sucrose and 150 mM NaCl.

TABLE 3

Effect of Thermal Stabilizers on the Stability

| Thermal Stabilizer | Visual Appearance | Turbidity (OD 405 nm) | % Total REGN421 Recovered (RP-HPLC) | % Native REGN421 Recovered (SE-HPLC) | % REGN421 Aggregate Recovered (SE-HPLC) | % Native REGN421 Recovered (CEX-HPLC) |
|---|---|---|---|---|---|---|
| Starting Material* (no 45° C. incubation) | Pass | 0.00 | 100 | 97.7 | 1.0 | 58.4 |
| No Thermal Stabilizer | Fail | 0.00 | 100 | 94.0 | 2.0 | 41.0 |
| 150 mM NaCl | Pass | 0.01 | 100 | 91.4 | 4.4 | 44.7 |
| 150 mM NaCl + 10% Sucrose | Pass | 0.00 | 100 | 94.0 | 2.1 | 45.4 |
| 20% Sucrose | Pass | 0.00 | 98 | 94.5 | 1.2 | 40.8 |
| 20% Sorbitol | Pass | 0.04 | 99 | 92.9 | 2.6 | 26.9 |
| 10% Mannitol | Pass | 0.00 | 99 | 93.8 | 2.0 | 39.5 |
| 20% Trehalose | Pass | 0.00 | 99 | 94.7 | 1.2 | 40.2 |
| 5% Glycerol | Pass | 0.02 | 100 | 85.4 | 10.9 | NP |
| 3% Arginine | Fail | 0.02 | 100 | 90.1 | 5.7 | 42.7 |
| 3% Glycine | Pass | 0.01 | 106 | 91.1 | 5.0 | 31.9 |

For the antibody stability results shown in Table 3, 0.3 mL of 10 mM phosphate, pH 6.0, 0.2% Polysorbate 20, and 25 mg/mL REGN421, plus the indicated thermal stabilizer, in a 2 mL Type 1 borosilicate glass vial with a FluoroTec® coated 4432/50 butyl rubber stopper were subjected to 45° C. for 28 days. Turbidity was reported as the change in $OD_{405}$ relative compared to starting material. Starting material results represent the average results of the starting material for all ten formulations not incubated at 45° C. OD=Optical density; RP=Reverse phase high performance liquid chromatography; SE=Size exclusion high performance liquid chromatography; CEX=cation exchange high performance liquid chromatography.

Example 6: Stress Stability Studies or REGN421 Formulation

Accelerated stress studies were performed by holding REGN421 at 25° C. for 6 months. At this accelerated condition, a shift in the charge variant profile toward more acidic species was observed by cation exchange chromatography (CEX-HPLC). A 2% to 5% decrease in purity was observed by SDS PAGE after six months of storage, along with a 1.6% reduction in purity and a 1.2% increase in high molecular weight aggregate formation detected by SE-HPLC. There was no loss of potency of REGN421 as determined by binding assay after six months of storage at 25° C.

Additional accelerated and stress stability studies performed on REGN421 antibody indicate that the protein is physically stable when vortexed for 60 minutes or 120 minutes, frozen and thawed from −80° C. to ambient temperature for eight cycles, incubated at 45° C. for 28 days, incubated at 37° C. for 28 days, or incubated at 25° C. for 28 days (Table 4). During these studies, the solution remained visibly clear, no loss of protein was observed, and no change in pH occurred after these stresses. However, a decrease in the purity of REGN421 was detected by size exclusion HPLC and cation exchange HPLC when the protein was incubated at ≥25° C. for 28 days, indicating that changes in molecular weight and charge variants occur when REGN421 is exposed to stress conditions. A smaller level of chemical degradation was detected when the protein was incubated at 37° C. compared to incubation at 45° C. REGN421 was physically and chemically stable over the 14 day assessment period at 25° C. and after agitation and freeze/thaw cycles. No significant loss of potency, as determined using the Dll4/Notch binding assay, was observed for any of the stressed samples.

For the antibody stability results shown in Table 4, 0.3 mL of 10 mM Histidine, pH 6.0, 0.2% Polysorbate 20, 10% Sucrose, 150 mM NaCl, and 25 mg/mL HIH685P, in a 2 mL Type 1 borosilicate glass vial with a FluoroTec® coated 4432/50 butyl rubber stopper was combined with the organic cosolvents and subjected to the various designated stresses. Turbidity was reported as the relative change in OD at 405 nm as compared to the starting material. The acceptance criteria for the binding assay was 50-150% of reference standard. OD=Optical density; RP=Reverse phase high performance liquid chromatography; SE=Size exclusion high performance liquid chromatography; CEX=cation exchange high performance liquid chromatography.

REGN421 continued to meet the acceptance criteria for all the analyses after 24 months of storage at 5° C. See Table 5.

Example 8: Compatibility with IV Delivery Device

The 25 mg/mL REGN421 formulation was diluted in an intravenous (IV) bag composed of polyvinyl chloride (PVC) with Di-(2-ethylhexyl)-phthalate (DEHP) containing normal saline. Three different doses of REGN421 were examined in this study including a low dose (0.1 mg/kg and 40 kg patient), a middle dose (4 mg/kg and 40 kg patient), and a high dose (16 mg/kg and 120 kg patient). For the low dose, additional "placebo" was added to the bag to help stabilize the REGN421 against agitation.

TABLE 5

Stability of 25 mg/mL REGN421 (10 mM phosphate, pH 6.0, 0.2% polysorbate 20, 10% sucrose, and 150 mM NaCl)

| | Storage Temperature/duration | | | |
|---|---|---|---|---|
| | −80° C./ 24 mo. | −30° C./ 24 mo. | −20° C./ 12 mo. | 5° C./ 24 mo. |
| Appearance | Pass | Pass | Pass | Pass |
| pH | 6.1 | 6.1 | 5.9 | 5.9 |
| Turbidity (OD 405 nm)[1] | 0.00 | 0.00 | 0.00 | 0.00 |
| % Total REGN421 Recovered (RP-HPLC) | 105 | 105 | 99 | 105 |
| Purity by Size-Exclusion-HPLC | | | | |
| % main peak purity | 99.4 | 98.8 | 98.3 | 97.7 |
| % HMW species | 0.4 | 0.5 | NA | NA |
| Charged Variant Analysis by CE-HPLC | | | | |
| % region 1 (acidic) | 18 | 18 | NA | NA |
| % region 2 (main) | 57 | 57 | 59 | 58.3 |

TABLE 4

Stress Stability of 25 mg/mL Anti-Dll4 Antibody

| Stress Test | No Stress | Agitation | | 45° C. Incubation | | 37° C. Incubation | | 25° C. Incubation | | Freeze/ Thaw |
|---|---|---|---|---|---|---|---|---|---|---|
| Length of Stress | 0 | 60 min | 120 min | 14 days | 28 days | 14 days | 28 days | 14 days | 28 days | 8 cycles |
| Visual Appearance | Pass | Pass | Pass | Pass | Pass | Pass | Pass | Pass | Pass | Pass |
| Turbidity (OD 405 nm) | 0.00 | 0.00 | 0.00 | 0.00 | 0.00 | 0.00 | 0.00 | 0.00 | 0.01 | 0.00 |
| pH | 5.9 | 5.9 | 5.9 | 6.0 | 6.0 | 6.0 | 6.0 | 6.0 | 6.0 | 6.0 |
| % Total REGN421 Recovered (RP-HPLC) | 100 | 99 | 96 | 96 | 100 | 98 | 100 | 97 | 101 | 99 |
| % Native REGN421 Recovered (SE-HPLC) | 98.0 | 97.9 | 98.0 | 95.8 | 94.0 | 96.9 | 96.0 | 97.9 | 97.7 | 98.0 |
| % Native REGN421 Recovered (CEX-HPLC) | 58.4 | 58.7 | 59.4 | 52.2 | 45.4 | 55.5 | 51.5 | 59.3 | 57.7 | 58.8 |
| Binding Assay (% Relative Potency) | 89 | NP | 94 | NP | 88 | NP | 101 | NP | 94 | 88 |

Example 7: Storage Stability of Formulated Anti-Dll4 Antibody

No significant loss of REGN421 was observed by UV spectrophotometry, or as determined by SDS-PAGE, after 24 months of storage at −80° C., −30° C., or −20° C. A 0.8% decrease in purity and a 0.4% increase in aggregate formation were detected by SE-HPLC after storage at 5° C. for 24 months. There was no significant change in charge variants as detected by CEX HPLC after 24 months of storage at the tested conditions. There was no change in potency as determined by binding assay at the end of the storage period.

TABLE 5-continued

Stability of 25 mg/mL REGN421 (10 mM phosphate, pH 6.0, 0.2% polysorbate 20, 10% sucrose, and 150 mM NaCl)

| | Storage Temperature/duration | | | |
|---|---|---|---|---|
| | −80° C./ 24 mo. | −30° C./ 24 mo. | −20° C./ 12 mo. | 5° C./ 24 mo. |
| % region 3 (basic) | 25 | 25 | NA | NA |
| Binding Assay (% Ref. Std.) | 100 | 99 | 95.3 | NP |

The IV bags containing diluted REGN421 were first held for 24 hours at 5° C. and then held for and additional 24 hours at 25° C. After these incubations were complete, the IV bags were connected to infusion sets, primed with the diluted antibody, and held for one hour at ambient temperature. Diluted antibody was pumped through the infusion sets at rates ranging from 25 mL/hr to 500 mL/hr. Three infusion pumps and three infusion sets representing the major suppliers (Alaris, Baxter, and Hospira) were utilized in this investigation. These infusion sets represent all of the basic materials (PVC with DEHP, PVC with TriOctyl-TriMellitate (TOTM), and polyolefins) that comprise infusion sets with inline filters. All infusion sets contained a 0.2 µm polyethersulfone filter.

REGN421 was physically stable when held for 24 hours at 5° C., held for 24 hours at 25° C. (see Table 6), held for 1 hour at ambient temperature in the various infusion sets, and pumped through the infusion sets utilizing the various infusion pumps at a rate of either 25 mL/hr or 500 mL/hr. Precipitates were not detected by visual inspection or turbidity, the pH of the solution was stable, and there was no decrease in protein concentration as determined by RP-HPLC detected in any sample tested. The protein was also chemically stable. No increase in molecular weight species or charge variants were observed as determined by SE-HPLC and CEX-HPLC, respectively, in this compatibility study.

This data support the following conclusions: (a) REGN421 was stable following dilution of 4 mg of REGN421 in a 50 mL IV bag containing saline or dilution of 1920 mg of REGN421 in a 250 mL IV bag of saline. The saline containing IV bag of saline was composed of PVC containing DEHP. (b) Diluted REGN421 was stable following incubation in an IV bag for periods of up to 24 hours at 5° C. or 24 hours at 25° C. (c) Diluted REGN421 can be administered using an infusion pump. (d) Diluted REGN421 can be administered with an infusion set composed of either PVC containing DEHP, PVC containing TOTM, or polyolefin. (e) The use of an inline 0.2 µm polyethersulfone filter is compatible with REGN421. (f) Diluted REGN421 can be administered at a rate ranging from 25 mL/hr to 500 mL/hr.

Example 9: Molecular Mass Determination

Formulated REGN421 was characterized with respect to protein structure and activity. The predicted protein molecular weight of native REGN421 without glycosylation is approximately 146 kDa. Non-reducing SDS-PAGE was performed to confirm the molecular weight of the heterotetrameric molecule and to examine levels of high and low molecular weight protein forms that co-purified with the intact antibody. An alkylating reagent was adding during sample preparation to prevent disulfide shuffling and to minimize antibody degradation due to heating. The observed molecular weight of the glycosylated antibody determined following electrophoresis and Coomassie staining was observed to be approximately 150 kDa. The mass of REGN421 was also examined using SDS-PAGE under reducing conditions. Samples were reduced and heated prior to electrophoresis, and protein bands were detected by staining with Coomassie blue. REGN421 was detected as two main bands corresponding to the antibody heavy chain (approximately 50 kDa) and light chain (approximately 25 kDa).

Capillary electrophoresis-SDS (CE-SDS) was also employed to assess the mass of REGN421. CE-SDS is able

TABLE 6

| Saline IV Bag (mL) | REGN421 (mg) | IV Infusion Set | Total REGN421 recovered (mg/mL) | % Native (SE-HPLC) | % Main Charge Form (CEX-HPLC) |
|---|---|---|---|---|---|
| 100 | 8 | Alaris PVC w/DEHP | 0.059 | 97.6 | 60.3 |
| 100 | 8 | Baxter PVC w/TOTM | 0.060 | 97.3 | 61.8 |
| 100 | 8 | Hospira Polyethylene lined PVC | 0.061 | 97.4 | 61.3 |
| 100 | 160 | Alaris Low Sorbing Polyethylene lined PVC | 1.40 | 98.1 | 59.8 |
| 100 | 160 | Baxter PVC w/DEHP | 1.51 | 97.5 | 60.3 |
| 100 | 160 | Hospira PVC w/TOTM | 1.41 | 97.7 | 59.9 |
| 250 | 1920 | Alaris Polypropylene | 6.87 | 97.7 | 60.6 |
| 250 | 1920 | Baxter PVC w/TOTM | 6.85 | 97.9 | 60.4 |
| 250 | 1920 | Hospira PVC w/DEHP | 6.77 | 98.0 | 60.2 | to resolve reduced IgG polypeptide chains by size and allows for quantification of the heterogeneity and variants that may exist in REGN421 antibody. The percentage of non-glycosylated heavy chain is calculated from the ratio of corrected peak area of non-glycosylated heavy chain to the sum of the corrected peak areas corresponding to non-glycosylated and glycosylated heavy chains. Two principal peaks were observed in the CE-SDS reducing electropherograms for REGN421 antibody. The two principal peaks for drug substance lots align with two principal peaks identified as the reduced light (LC) and glycosylated heavy (HC) chains in the IgG control standard. The molecular weights of peaks labeled HC and LC for REGN421 and the IgG control standard are approximately 60 kDa and 25 kDa, respectively. The molecular weights of the heavy and light chains determined by this method are slighter greater than expected for human IgG1, suggesting that this technique may slightly overestimate the molecular weights of the heavy and light chains. The relative abundance of the non-glycosylated heavy chain (NGHC) form of the tested lots of REGN421 represent approximately 1.5% of the total peak area detected.

Example 10: Fucosylation Analysis

REGN421 drug substance lots were treated with PNGase F to release N-linked oligosaccharides from the antibody heavy chain. Free oligosaccharides were subsequently derivatized at the reducing end with the fluorescent reagent, anthranilic acid. Modified oligosaccharides were analyzed by reverse phase HPLC and MALDI-TOF mass spectrometry. Examination of the HPLC chromatogram revealed that the modified oligosaccharides were separated into two main groups, non-fucosylated bi-antennary species and fucosylated bi-antennary species. Within each group (fucosylated vs non-fucosylated), the oligosaccharides were further separated into digalactosyl (G2), monogalactosyl (G1) or agalactosyl (G0) forms. Oligosaccharide structure assignments were achieved through the mass analysis of each fractionated oligosaccharide using MALDI-TOF mass spectrometry. REGN421 lots that were analyzed contained between 82.4 and 87.0% (84.6%±1.47%; av±SD) of fucosylated oligosaccharide chains (Table 7), based on the integration of corresponding peaks in the chromatograms. Mass analysis of pooled oligosaccharides demonstrated that fucosylated bi-antennary oligosaccharides are the dominant species, which agrees with the HPLC analysis. The observed difference in the amount of galactosylation within the N-linked sugar chains between various tested lots of REGN421 reflects the heterogeneity that can occur during antibody production.

Example 11: Heavy Chain C-Terminal Lysine Analysis

Peptide mapping was used to confirm the C-terminal sequence of REGN421. REGN421 was denatured in 6.0 M urea, 100 mM Tris, pH 7.5, reduced with 5 mM DTT and alkylated with 12.5 mM iodoacetamide. The protein was then diluted 6-fold to bring the urea concentration down to 1.0 M, and subsequently digested with trypsin (1:20 enzyme to substrate ratio) at 37° C. for three hours. Peptides were separated by HPLC and analyzed by mass spectroscopy. As standards for identification of the native C-terminal peptide from REGN421, three synthetic peptides corresponding to the three most likely putative C-terminal peptide sequences (SLSLSP, SLSLSPG, and SLSLSPGK; respectively SEQ ID NO: 10, SEQ ID NO: 11, and SEQ ID NO: 12) were generated and analyzed by HPLC using an identical solvent elution gradient compared to the gradient used to elute the REGN421 trypsin digested peptides to facilitate the identification of the actual C-terminal peptide in the tryptic map of REGN421. The expected trypsin derived C-terminal peptide of SLSLSPGK (SEQ ID NO:12) was not found in the tryptic maps of any of the tested REGN421 lots, indicating that the C-terminal Lys was removed. In the tryptic map, there is only one peptide (elution at 46.60 min) that co-eluted with one of the synthetic peptides (SLSLSPG; SEQ ID NO:11). This peptide corresponds to the C-terminal peptide of REGN421 heavy chain through mass analysis (expected mass 659.69, observed mass 660.2). The results suggest that post-translational processing leads to complete removal of the expected Lys from the heavy chain C-terminus.

TABLE 7

REGN421 Glycosylation Patterns

| | Glycan Form | Lot 1 | Lot 2 | Lot 3 | Lot 4 | Lot 5 | Glycan Formulae |
|---|---|---|---|---|---|---|---|
| Nonfucosylted | G0 (%) | 6.9 | 7.1 | 7.9 | 5.2 | 3.8 | $(GlcNAc)_2(Man)_3(GlcNAc)_2$ |
| | G1 (%) | 3.3 | 3.9 | 4.3 | 3.9 | 3.7 | $(GlcNAc)_2(Man)_3(GlcNAc)_2(Gal)_1$ |
| | G2 (%) | 0.9 | 0.8 | 1.0 | 1.8 | 2.1 | $(GlcNAc)_2(Man)_3(GlcNAc)_2(Gal)_2$ |
| | Man-5 (%) | 4.5 | 3.5 | 4.0 | 4.6 | 3.6 | $(GlcNAc)_2(Man)_5$ |
| Fucosylated | G0F (%) | 36.8 | 37.2 | 35.9 | 29.4 | 25.2 | $Fuc(GlcNAc)_2(Man)_3(GlcNAc)_2$ |
| | G1F (%) | 37.1 | 37.3 | 36.0 | 40.7 | 45.0 | $Fuc(GlcNAc)_2(Man)_3(GlcNAc)_2(Gal)_1$ |
| | G2F (%) | 10.4 | 10.3 | 10.9 | 14.3 | 16.7 | $Fuc(GlcNAc)_2(Man)_3(GlcNAc)_2(Gal)_2$ |
| % Fucosylation | | 84.3 | 84.8 | 82.8 | 84.4 | 86.9 | |

What is claimed is:

1. A pharmaceutical formulation consisting of
   (a) 25 mg/mL±3.75 mg/mL of an anti-Dll4 antibody comprising the HCVD of SEQ ID NO: 1 and the LCVD of SEQ ID NO: 5,
   (b) 10 mM±3 mM phosphate, pH 6±0.5,
   (c) 0.2%±0.03% polysorbate 20,
   (d) 150 mM±22.5 mM sodium chloride, and
   (e) 10%±1.5% sucrose, in water
   wherein the antibody a molecular weight of about 150 kDa; and about 82% to about 87% of the antibodies are fucosylated.

2. A pharmaceutical composition of claim 1, wherein said composition is contained in a container.

3. The pharmaceutical composition of claim 2, wherein the container is a vial.

4. The pharmaceutical composition of claim 3, wherein the vial is glass.

5. The pharmaceutical composition of claim 2, wherein the container is an IV drip bag.

6. The pharmaceutical composition of claim 5, wherein the bag is made of polyvinyl chloride.

7. The pharmaceutical composition of claim 5, wherein the bag is made of poly olefin.

8. A kit comprising a pharmaceutical composition of claim 1, a container, and instructions.

9. The kit of claim 8, wherein the container is a glass vial fitted with a fluorocarbon-coated 4023/50 rubber stopper.

10. The pharmaceutical formulation of claim 1, wherein after 28 days of storage at 45° C., at least 94% of the antibody has native conformation, or at least 45% of the antibody is the main charge form.

11. The pharmaceutical formulation of claim 1, wherein after 28 days of storage at 25° C., at least 97% of the antibody has native conformation, or at least 57% of the antibody is the main charge form.

12. The pharmaceutical formulation of claim 1, wherein after 28 days of storage at 37° C., at least 97% of the antibody has native conformation, or at least 51% of the antibody is the main charge form.

13. The pharmaceutical formulation of claim 1, wherein after six months of storage at 5° C., at least 98% of the antibody has native conformation, at least 61% of the antibody is the main charge form, or the antibody retains about 100% of the potency of the antibody prior to storage.

14. The pharmaceutical formulation of claim 1, wherein after six months of storage at −80° C., at least 99% of the antibody has native conformation, at least 57% of the antibody is the main charge form, or the antibody retains about 100% of the potency of the antibody prior to storage.

15. The pharmaceutical formulation of claim 1, wherein after six months of storage at −30° C., at least 99% of the antibody has native conformation, at least 57% of the antibody is the main charge variant, or the antibody retains at least 65% of the potency of the antibody prior to storage.

16. The pharmaceutical formulation of claim 1, wherein after six months of storage at −20° C., at least 98% of the antibody has native conformation, at least 60% of the antibody is the main charge variant, or the antibody retains about 100% of the potency of the antibody prior to storage.

* * * * *

SEQUENCE LISTING

<160> NUMBER OF SEQ ID NOS: 12

<210> SEQ ID NO 1
<211> LENGTH: 123
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Phe Leu Trp Tyr Asp Gly Thr Asn Lys Asn Tyr Val Glu Ser Val
    50                  55                  60

Lys Gly Arg Phe Thr Ile Ser Arg Asp Asn Ser Lys Asn Met Leu Tyr
65                  70                  75                  80

Leu Glu Met Asn Ser Leu Arg Ala Glu Asp Thr Ala Val Tyr Tyr Cys
                85                  90                  95

Ala Arg Asp His Asp Phe Arg Ser Gly Tyr Glu Gly Trp Phe Asp Pro
            100                 105                 110

Trp Gly Gln Gly Thr Leu Val Thr Val Ser Ser
        115                 120

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Phe Thr Phe Ser Ser Tyr Gly
 1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Leu Trp Tyr Asp Gly Thr Asn Lys
 1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Ala Arg Asp His Asp Phe Arg Ser Gly Tyr Glu Gly Trp Phe Asp Pro
 1               5                  10                  15

<210> SEQ ID NO 5
<211> LENGTH: 107
<212> TYPE: PRT

<213> ORGANISM: Artificial Sequence
<220> FEATURE:
<223> OTHER INFORMATION: Synthetic

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln His Arg Ser Asn Trp Pro Pro
                85                  90                  95

Thr Phe Gly Gly Gly Thr Lys Val Glu Ile Lys
            100                 105

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Gln Ser Val Ser Ser Tyr
1               5

<210> SEQ ID NO 7
<211> LENGTH: 3
<212> TYPE: PRT
<213> ORGANISM: Artificial Sequence
<220> FEATURE:
<223> OTHER INFORMATION: Synthetic

<400> SEQUENCE: 7

Asp Ala Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Gln His Arg Ser Asn Trp Pro Pro Thr
1               5

<210> SEQ ID NO 9
<211> LENGTH: 685
<212> TYPE: PRT
<213> ORGANISM: Homo sapiens

<400> SEQUENCE: 9

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

```
Gln Leu Gln Glu Phe Ile Asn Glu Arg Gly Val Leu Ala Ser Gly Arg
         35                  40                  45

Pro Cys Glu Pro Gly Cys Arg Thr Phe Arg Val Cys Leu Lys His
 50                  55                  60

Phe Gln Ala Val Val Ser Pro Gly Pro Cys Thr Phe Gly Thr Val Ser
 65                  70                  75                  80

Thr Pro Val Leu Gly Thr Asn Ser Phe Ala Val Arg Asp Asp Ser Ser
                 85                  90                  95

Gly Gly Gly Arg Asn Pro Leu Gln Leu Pro Phe Asn Phe Thr Trp Pro
             100                 105                 110

Gly Thr Phe Ser Leu Ile Ile Glu Ala Trp His Ala Pro Gly Asp Asp
         115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445
```

Cys Ala His Gly Gly Thr Cys His Asp Leu Glu Asn Gly Leu Met Cys
        450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 10
<211> LENGTH: 6
<212> TYPE: PRT
<213> ORGANISM: Artificial Sequence
<220> FEATURE:
<223> OTHER INFORMATION: Synthetic

<400> SEQUENCE: 10

Ser Leu Ser Leu Ser Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Ser Leu Ser Leu Ser Pro Gly
1               5

<210> SEQ ID NO 12
<211> LENGTH: 8
<212> TYPE: PRT

```
<213> ORGANISM: Artificial Sequence
<220> FEATURE:
<223> OTHER INFORMATION: Synthetic

<400> SEQUENCE: 12

Ser Leu Ser Leu Ser Pro Gly Lys
 1               5
```